(12) United States Patent
Lin et al.

(10) Patent No.: US 9,289,455 B2
(45) Date of Patent: Mar. 22, 2016

(54) METHOD OF ENHANCING HYALURONIC ACID SECRETION USING PROBIOTIC STRAIN

(71) Applicant: TCI Co., Ltd., Taipei (TW)

(72) Inventors: Yung-Hsiang Lin, Taipei (TW); Hsiang-Ling Su, Taipei (TW); Chin-Hsiu Yu, Taipei (TW)

(73) Assignee: TCI Co., Ltd., Taipei (TW)

( * ) Notice: Subject to any disclaimer, the term of this patent is extended or adjusted under 35 U.S.C. 154(b) by 0 days.

(21) Appl. No.: 14/670,060

(22) Filed: Mar. 26, 2015

(65) Prior Publication Data

US 2015/0290257 A1      Oct. 15, 2015

(30) Foreign Application Priority Data

Apr. 11, 2014   (TW) .............................. 103113465 A

(51) Int. Cl.
*A61K 35/744*   (2015.01)
*C12R 1/46*     (2006.01)

(52) U.S. Cl.
CPC ................. *A61K 35/744* (2013.01); *C12R 1/46* (2013.01)

(58) Field of Classification Search
CPC ............................... A61K 35/744; C12R 1/46
See application file for complete search history.

*Primary Examiner* — Louise W Humphrey
*Assistant Examiner* — Stephen A Perkins
(74) *Attorney, Agent, or Firm* — WPAT, P.C.; Anthony King

(57) ABSTRACT

The present invention provides a method of enhancing hyaluronic acid secretion in a subject, which comprises administrating a composition containing of *Streptococcus thermophilus* DSM 28121 to the subject, and the hyaluronic acid content in the blood of the subject is increased. The present invention further provides a novel probiotic strain which is *Streptococcus thermophilus* DSM 28121, which has the ability to survive and colonize in the intestine of the subject to increase the number.

19 Claims, 4 Drawing Sheets

METHOD OF ENHANCING HYALURONIC ACID SECRETION USING PROBIOTIC STRAIN

CROSS-REFERENCE TO RELATED APPLICATIONS

This application claims the priority of Taiwanese patent application No. 103113465, filed on 11 Apr. 2014, which is incorporated herewith by reference.

BACKGROUND OF THE INVENTION

1. Field of the Invention

The invention relates to a novel probiotic strain, more particularly methods of enhancing hyaluronic acid secretion using the probiotic strain.

2. The Prior Arts

Hyaluronic acid (hyaluronate; HA) is a liner glycosaminoglycan chain composed of many repeating units of the disaccharide, D-glucuronic acid and N-acetylglucosamine, it is distributed widely throughout connective, epithelial, and neural tissues. In addition, one of the chief components of the extracellular matrix, hyaluronic acid contributes significantly to cell proliferation and migration, may also be involved in the progression of some malignant tumors.

In the human body, hyaluronic acid occurs in the salt hyaluronate form and is found in high concentrations in the skin, umbilical cord, and vitreous humor. The average 70 kg (154 lbs) person has roughly 15 grams of hyaluronic acid in the body, however, hyaluronic acid content in the human body tends to gradually decrease with aging, and is lost almost every day. So babies are born with a high level of hyaluronic acid content, 65% hyaluronic acid remains at the age 25, and only 25% hyaluronic acid remains at the age 60. Therefore, young skin is soft and elastic. The skin gradually reduces water retention capacity as the hyaluronic acid is lost. In addition to age, modern people are more likely to lose skin moisture and also need to supply hyaluronic acid due to the factors of excessive work pressure, irregular life, unbalanced diet, ultraviolet, working long-term in an air conditioned office.

Recent reports have shown that hyaluronic acid improves skin hydration, stimulates production of collagen in skin, works as an antioxidant and free radical scavenger, maintains skin elasticity, cushions joints and nerve tissues, has an antibacterial and anti-inflammatory activity and maintains the fluid in the eye tissues, which may help to protect against numerous possible eye concerns. Therefore, HA loss in eye will result in dry eyes and eyestrain; HA loss in synovial fluid will result in decreasing the protection for joints.

Hyaluronic acid has the highest hygroscopic, viscoelastic, non-antigenic, biodegradable and biocompatible properties, therefore, it has found a number of applications in medicine, cosmetics and specialty foods. Hyaluronic acid is obtained commercially from rooster combs. However, hyaluronic acid extracted from rooster combs applied in the food will have the cross-species zoonotic disease concerns; it is less effective through food intake due to digestive passage.

SUMMARY OF THE INVENTION

To solve the problem, the present invention provides the method of use of a novel probiotic strain, which was deposited in the Deutsche Sammlung von Mikroorganismen and Zellkulturen GmbH (DSMZ) located at Inhoffenstr. 7B D-38124 Braunschweig with an accession number DSM 28121 on Dec. 2, 2013.

The present invention provides a method of enhancing hyaluronic acid secretion in a subject comprising administrating a composition containing a dose of *Streptococcus thermophilus* DSM 28121 to the subject, wherein the dose comprises $10^3$ CFU to $10^{12}$ CFU of *Streptococcus thermophilus* DSM 28121.

In one embodiment, the *Streptococcus thermophilus* DSM 28121 is isolated from breast milk.

In one embodiment, the *Streptococcus thermophilus* DSM 28121 is a probiotic strain.

In one embodiment, the *Streptococcus thermophilus* DSM 28121 is administrated orally.

In one embodiment, the *Streptococcus thermophilus* DSM 28121 has the ability to survive and colonize in the intestine of the subject to increase the number.

In one embodiment, the hyaluronic acid content in the blood of the subject is increased.

In one embodiment, the *Streptococcus thermophilus* DSM 28121 is active or inactive.

In one embodiment, the composition is a food product, a health supplement, a medicament or a skin care product.

In one embodiment, the composition further comprises a metabolite of *Streptococcus thermophilus* DSM 28121.

In one embodiment, the skin hydration in the subject is increased, and the condition of dry eye, arthroncus, arthralgia and ankylosis in the subject is improved.

The present invention provides a method of enhancing hyaluronic acid content in the blood in a subject comprising administrating a composition having a dose of *Streptococcus thermophilus* DSM 28121 to the subject, wherein the dose comprises $10^3$ CFU to $10^{12}$ CFU of *Streptococcus thermophilus* DSM 28121.

The present invention also provides an isolated probiotic strain of *Streptococcus thermophilus* deposited in the Deutsche Sammlung von Mikroorganismen and Zellkulturen GmbH (DSMZ) with an accession number DSM 28121.

In summary, the present invention provides a method of using a probiotic strain of *Streptococcus thermophilus* DSM 28121 isolated from human breast milk for producing hyaluronic acid. The probiotic strain of *Streptococcus thermophilus* DSM 28121 has the bile salt resistance and stomach acid resistance, the intestinal cell adsorption capacity and the ability to be transported to the intestine while keeping good activity. The probiotic strain also has the ability of proliferation in the intestine to increase the number of strains, and the efficacy of inhibiting allergic reaction, anti-inflammatory and modulating lymphocyte activity. Most important of all, the probiotic strain of the present invention has excellent efficacy of producing hyaluronic acid in the intestine, it can enhance the hyaluronic acid content in human body after administration. Therefore, the probiotic strain of the present invention or its metabolites can be applied in a food product, a health supplement, a medicament or a skin care product, which can enhance hyaluronic acid, and improve skin, eye and joint health in human body.

The detailed technology and above preferred embodiments implemented for the present invention are described in the following paragraphs accompanying the appended drawings for people skilled in this field to well appreciate the features of the claimed invention.

DETAILED DESCRIPTION OF THE PREFERRED EMBODIMENT

Figure 1:
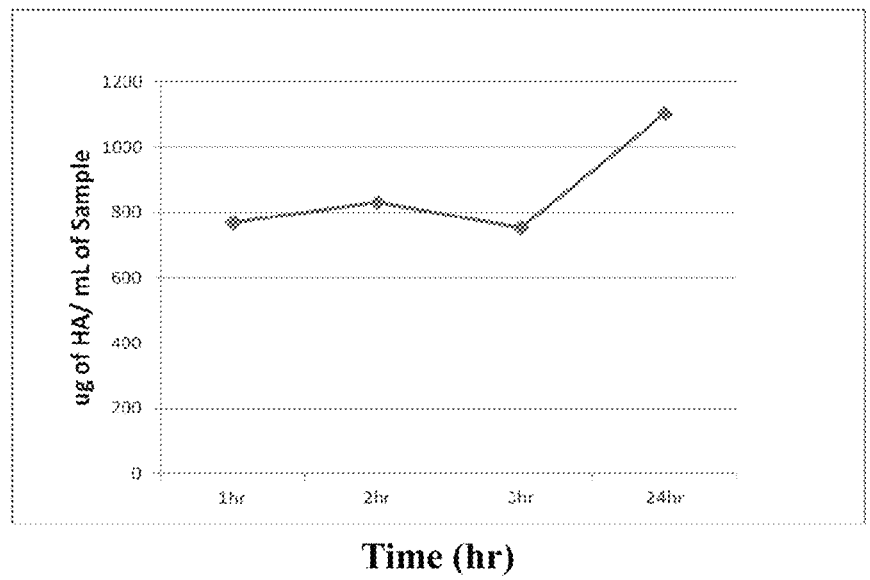
FIG. 1 shows that the hyaluronic acid content produced by *Streptococcus thermophilus* DSM 28121 culturing in the artificial intestinal solution at different time.

Probiotic strain is a microorganism, bacteria, hybrid strain, extract or metabolite having a positive effects on a host, derived from the human body is a live microorganism in the intestinal tract to confer health benefits. Humans also can take the probiotic strain for health benefits by supplement. The metabolites of the probiotic strain refer to the secretion of the strain, and the culture medium after fermentation is included.

The present invention provides a bacterial strain isolated from human breast milk. After purification, culture and identification, it is a novel probiotic strain to be deposited in the Deutsche Sammlung von Mikroorganismen and Zellkulturen GmbH (DSMZ) with an accession number DSM 28121. The strain having the ability of producing hyaluronic acid in intestine is found by artificial intestinal solution experiment. The result shows that the probiotic strain has the absorption capacity to the intestinal epithelial cells, the efficacy of maintaining skin elasticity, lubricating and cushioning joints, and it can be manufactured into a food product, a health supplement, a medicament or a skin care product for effectively enhancing hyaluronic acid in the human body.

Analysis of Hyaluronic Acid Using Carbazole Method

The cultured medium to be analyzed is washed 3 times with 4 volumes of 95% EtOH to precipitate out the non-sugar components. The supernatant is then re-dissolved in 1 volume of water for further analysis. Hyaluronic acid content is measured by carbazole method (Bitter and Muir, 1962, Anal Biochem. 4:330-334). Hyaluronic acid is first hydrolysed with sulfuric acid to unstable hexuronic acid which will react with carbazole reagent to form pink colors. D-glucuronic acid is used as standard. 0.25 mL of the standard, sample, or blank solution is added respectively to each tube on ice. Then 1.5 mL sulfuric acid reagent with sodium tetraborate is added slowly to each tube and mixed well. The tubes are then moved to boiling water bath for 10 minutes. After cooling down to room temperature, 50 L of carbazole reagent is added to each tube. Bring all the tubes to boiling water bath for 5 minutes and let cool down to room temperature. The optical density of each reaction is measured at wavelength of 525 nm. The formula for calculating hyaluronic acid content in one gram of probiotic strain is as following: hyaluronic acid content in one gram of probiotics=(Abs.−0.073)/0.006)×100)×2.07)/((20/100)) the abbreviation or values are represented as following: Abs.=absorption of probiotics 100=100 times dilution 2.07=conversion coefficient 20/100=the ratio of the probiotics powder/solution EXAMPLE 1 Isolating the probiotic strain from breast milk.

EXAMPLE 1

Isolating the Probictic Strain from Breast Milk

*Streptococcus thermophilus* DSM 28121 is isolated from healthy human breast milk. Adequate dilutions of the fresh breast milk samples are spread on MRS-Cys agar plates for isolation of *lactobacilli* spp. and *Streptococcus* spp. The plates were incubated for 48 h at 37° C. in anaerobic conditions. After incubation and counting, between 5 and 10 isolates from were selected from the agar plate including at least 1 representative of each colony morphology type. They were observed by optical microscopy to determine their morphology and Gram staining.

EXAMPLE 2

Screening of Bacteria Strain 2.1 Biochemical Identification

Gram's stain used to classify bacteria in which a bacterial specimen is first stained with crystal violet, then treated with an iodine solution, decolorized with alcohol, and counterstained with safranine.

2.2 Molecular Identification 16S rDNA sequences are very little difference in the same bacterial species because each distinct microbial species has unique DNA sequences, therefore, the present invention uses 16S rDNA to identify the bacterial species, The present invention identifies the isolated bacterial species by using broad-range 16S rDNA polymerase chain reaction (Simo Nikkari, Fred A. Lopez et al., Emerging Infectious Disease Journal 2002, 8, 188-194). The isolated bacteria colonies were collected and the DNA extracted using TACO™ Total DNA Extraction Kit (GeneReach, Taiwan). The 16S rDNA sequences of bacteria were analyzed with PCR methods using the universal primer as following: fD1 mod (5'-AGAGTTTGATCYTGGYTYAG-3 SEQ ID NO:1) and 16S1RR-B (5'-CTTTACGCCCARTRAWTCCG-3 SEQ ID NO:2); 63F (5'-CAGGCCTAACACATGCAAGTC-3', SEQ ID NO:3) and 16S1RR-B (5'-CTTTACGCCCAR-TRAWTCCG-3 SEQ ID NO:2); 8F2 (5'-TG-GAGAGTTTGATCCTGGCTCAG-3 SEQ ID NO:4) and 806R (5'-GGACTACCAGGGTATCTAAT-3 SEQ ID NO:5); and 515F (5'-GTGCCAGCAGCCGCGGTAA-3 SEQ ID NO:6) and 13R (5'-AGGCCCGGGAACGTATTCAC-3', SEQ ID NO:7). Reactions based on these primers contained 10 mM Tris-HCl pH 8.3, 50 mM KCl, 1.5 mM $MgCl_2$, 200 µM each deoxynucleoside triphosphates, 2.5 U AmpliTaq LD DNA polymerase (PE Biosystems, Foster City, Calif.), and 5-µL template, as well as 20 pmol of each primer in a total volume of 50 µL. After a denaturation step of 3 min at 94° C., PCR steps at 94° C. for 30 sec, 56° C. for 30 sec, and 72° C. for 30 sec were repeated 30 to 36 times, followed by an elongation step at 72° C. for 7 min in a GeneAmp PCR system 2400 thermal cycler (PE Biosystems). Products were detected by agarose gel electrophoresis and DNA staining with ethidium bromide. Then, PCR products were sequenced directly, as well as after cloning, by using the TA or TOPO cloning systems (INVITROGEN, USA). Automated ABI PRISM 373 or 377 DNA sequencers (INVITROGEN, USA)

and ABI PRISM™ BigDye™ Terminator Cycle Sequencing Ready Reaction kit (INVITROGEN, USA) were used for determining DNA sequences. Both DNA strands were analyzed, and base-editing was performed together with manual review of the electropherograms, using AutoAssembler (INVITROGEN, USA). The 16S rDNA sequences were compared with those in the GenBank database by using the BLAST search tool, confirming the strain is *Streptococcus thermophilus* (SEQ ID NO:8), which was deposited in the Deutsche Sammlung von Mikroorganismen and Zellkulturen GmbH (DSMZ) with an accession number DSM 28121 on Dec. 2, 2013.

The glycerol stock of *Streptococcus thermophilus* DSM 28121 was inoculated (1%, v/v) to MRS broth to culture for 16 to 24 hr and transfer to following culture medium at 5% (v/v) inoculation rate. The culture medium is included 20 to 60 g/L glucose, 5 to 30 g/L Sucrose, 10 to 20 g/L Yeast Extract, 5 to 10 g/L peptone, 2.5 to 8 g/L $K_2HPO_4$, 1 to 2 g/L NaCl and 0.5 to 1.2 g/L $MgSO_4.7H_2O$. The culture was incubated at 37° C. for 48 hrs before further analysis.

EXAMPLE 3

Artificial Intestinal Solution (AIS) Module (In Vitro)

Figure 2:
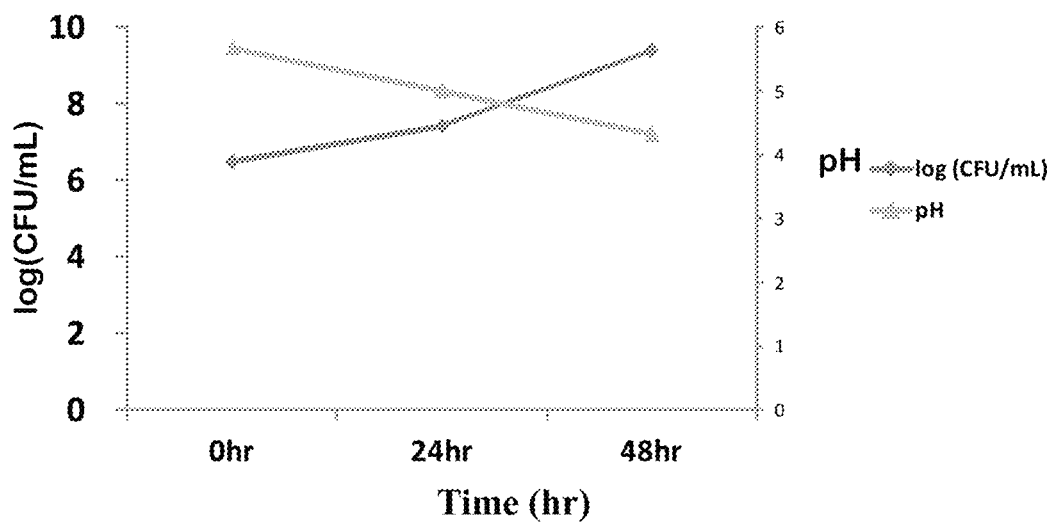
FIG. 2 shows the colony numbers and pH values of *Streptococcus thermophilus* DSM 28121 culturing in the artificial intestinal solution at different times.

The artificial intestinal solution (AIS) is made based on the formulation proposed by Hasjim et al. (Jovin Hasjim, Gautier Cesbron Lacau et at., Biomacromolecules 2010, 11, 3600-3608) with modifications. In the embodiment, the artificial intestinal solution is included digestive enzymes include 8 mg/mL pancreatin, 13 U/mL a-amylase and 1.12 U/mL amyloglucosidase are added to 0.2M acetate buffer (0.49 mM $MgCl2$, 200 mM $CaCl2$, pH6.0). The sterilized MRS broth is then added to AIS that mimics the general food intake as nutrients for bacterial growth in the intestine. The inoculation of *Streptococcus thermophilus* DSM 28121 is at human body temperature 37±° C. to create the artificial intestinal environment. The cultured medium is collected at various time point to monitor the bacterial growth and HA production. The growth of bacterial culture is measured using conventional plate count method. The culture is collected at various time points, diluted and transferred to MRS agar plate for colony count. As shown in FIG. 1, HA production of *Streptococcus thermophilus* DSM 28121 in AIS is at its highest amount at 24 hrs after inoculation, and the number of colonies is most numerous at the same time. As shown in FIG. 2, the decrease of pH indicates the growth of the acid-producing probiotics which is in accordance to the plate count from the culture in AIS.

In the present invention, the probiotic strain of *Streptococcus thermophilus* DSM 28121 isolated from breast milk has the ability of producing hyaluronic acid. The hyaluronic acid yield of one gram *Streptococcus thermophilus* DSM 28121 identified by above-mentioned carbazole method is 72.74 mg.

EXAMPLE 4

Clinical Trials (In Vivo)

To evaluate the efficacy of *Streptococcus thermophilus* DSM 28121 from breast milk on skin, eye, joint health, and the HA content in the blood. 4.1 The effect on the hyaluronic acid content in the blood and skin 4.1 the Effect on the Hyaluronic Acid Content in the Blood and Skin The clinical trial was conducted on 8 testers (n=8) aged from 25 to 40 years old who were administrated *Streptococcus thermophilus* DSM 28121 capsules at dosage of $10^3$ CFU to $10^{12}$ CFU/cap twice a day (in the morning and evening) for 28 days. And 3 testers (n=3) in the control group ingested capsules containing no *Streptococcus thermophilus* DSM 28121 a day.

The blood HA level was determined using Human Hyaluronic Acid (HA) ELISA Kit (CUSABIO CSB-E04805h, China) at day 0 and 28. To the pre-coated plate, 100 μL of standards and samples were added per well and covered with adhesive strip provided. The plate was then incubated for 2 hours at 37° C. and the liquid of each well was removed. To each well 100 μL of Biotin-antibody (1×) was added and covered with new adhesive strip for 1 hour incubation at 37° C. Then each well was aspirated and washed for 3 times with wash buffer and let stand for 2 minutes. To each well 100 μL of HRP-avidin (1×) was added and covered with new adhesive strip for 1 hour incubation at 37° C. Repeat the aspiration/wash process for five times. 90 mL of TMB substrate was added to each well and incubate without light for 15 to 30 minutes at 37° C. To end the reaction 50 μL of Stop Solution was added to each well and the optical density was measured within 5 minutes using spectrophotometer at 450 nm.

Figure 3:
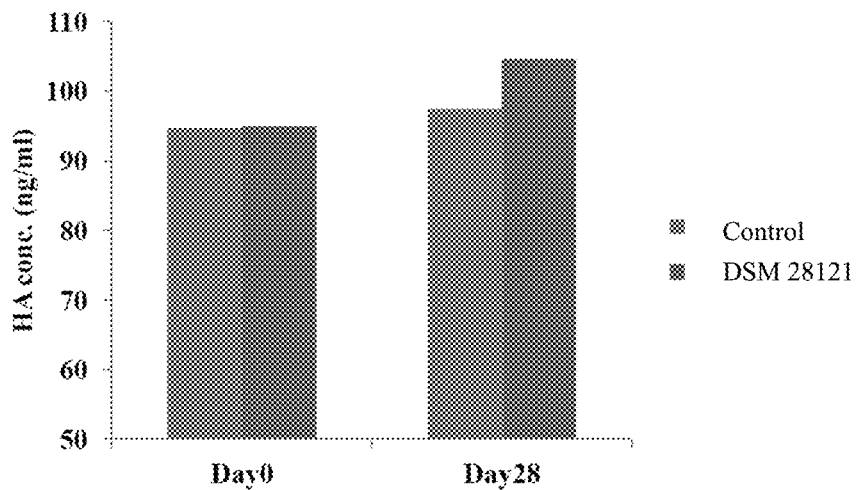
FIG. 3 illustrates the hyaluronic acid content in the blood of the testers (n=8) administrated *Streptococcus thermophilus* DSM 28121 capsules at day 0 and 28.

After ingesting *Streptococcus thermophilus* DSM 28121 capsules for 28 days, as shown in FIG. 3, average HA concentration was increased 10.2% related to that on day 0, and increased 7.3% compared to that of the control group on day 28. The population ratio of testers who had effective improvement on HA content was 5/8. The hyaluronic acid content in the blood of the testers administrated *Streptococcus thermophilus* DSM 28121 capsules was significantly increased.

Figure 4:
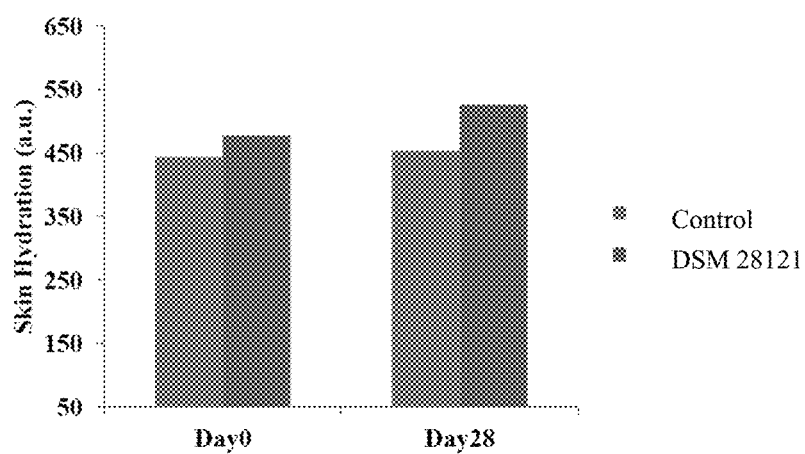
FIG. 4 illustrates the skin hydration on the testers (n=8) administrated *Streptococcus thermophilus* DSM 28121 capsules at day 0 and 28.

After ingesting *Streptococcus thermophilus* DSM 28121 capsules for 28 days, the skin hydration was determined using Skin Analyzer (DERMALAB COMBO, CORTEX TECHNOLOGIES, Denmark). As shown in FIG. 4, skin hydration increased 10.1% related to that on day 0, and increased 8.0% compared to that of the control group on day 28. The population ratio of subjects who had effective improvement on skin hydration was 6/8. The skin hydration of the testers administrated *Streptococcus thermophilus* DSM 28121 capsules was also significantly increased.

4.2 The Effect on Eye

The clinical trial was conducted on 8 testers (n=8) aged from 25 to 40 years old who were administrated *Streptococcus thermophilus* DSM 28121 capsules at dosage of $10^3$ CFU to $10^{12}$ CFU/cap twice a day (in the morning and evening) for 28 days.

Figure 5:
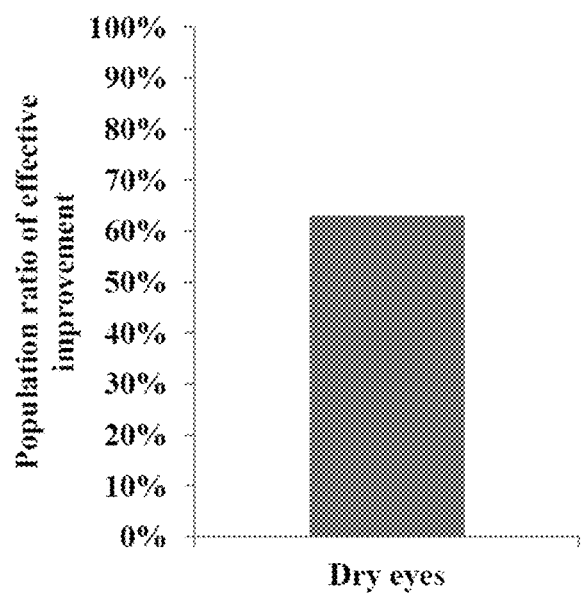
FIG. 5 illustrates the population ratio of effective improvement on eyes in the testers (n=8) administrated *Streptococcus thermophilus* DSM 28121 capsules at 28.
Figure 6:
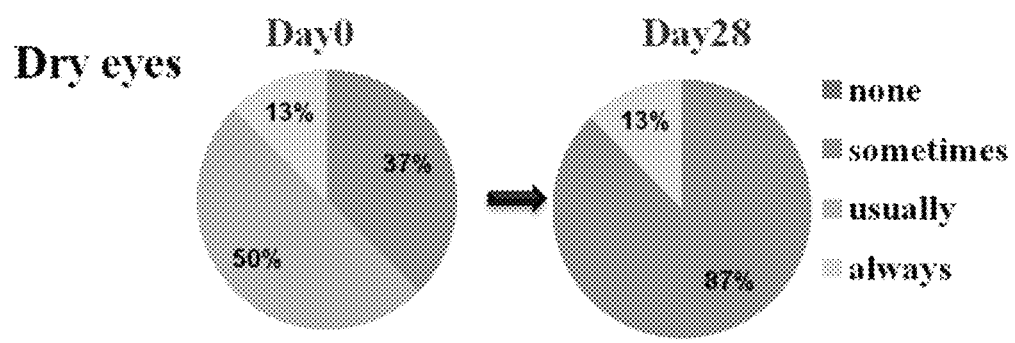
FIG. 6 illustrates the condition of dry eyes in the testers (n=8) administrated *Streptococcus thermophilus* DSM 28121 capsules at day 0 and 28.

The effects on dry eyes were investigated by questionnaire on day 0 and 28 of the trial. As shown in FIG. 5, there were 63% testers who felt effective improvement after ingesting *Streptococcus thermophilus* DSM 28121 capsules for 28 days. As shown in FIG. 6, the frequencies of dry eyes feeling were obviously declined after 28-day consumption. The condition of dry eyes and eyestrain the testers administrated *Streptococcus thermophilus* DSM 28121 capsules has improved.

4.3 The Effect on Joint

The clinical trial was conducted on 5 testers (n=5) aged from 25 to 40 years old who were administrated *Streptococcus thermophilus* DSM 28121 capsules at dosage of $10^3$ CFU to $10^{12}$ CFU/cap twice a day (in the morning and evening) for 7 and 28 days.

Figure 7:
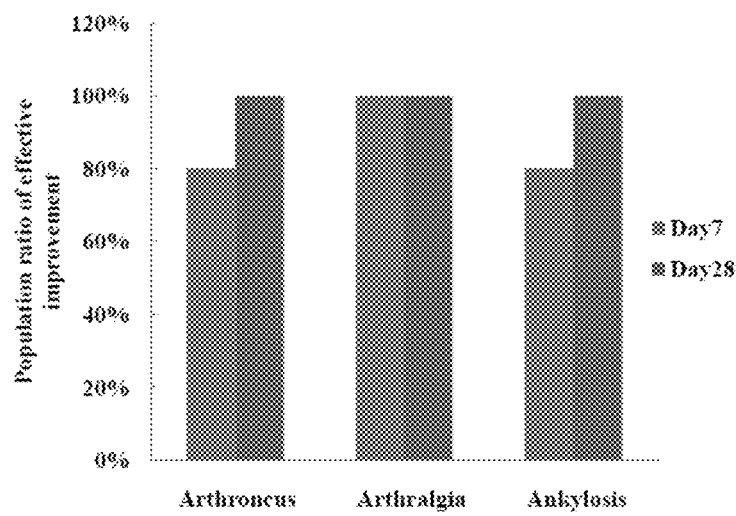
FIG. 7 illustrates the population ratio of effective improvement on arthroncus, arthralgia and ankylosis in the testers (n=5) administrated *Streptococcus thermophilus* DSM 28121 capsules at 7 and 28.
Figure 8:
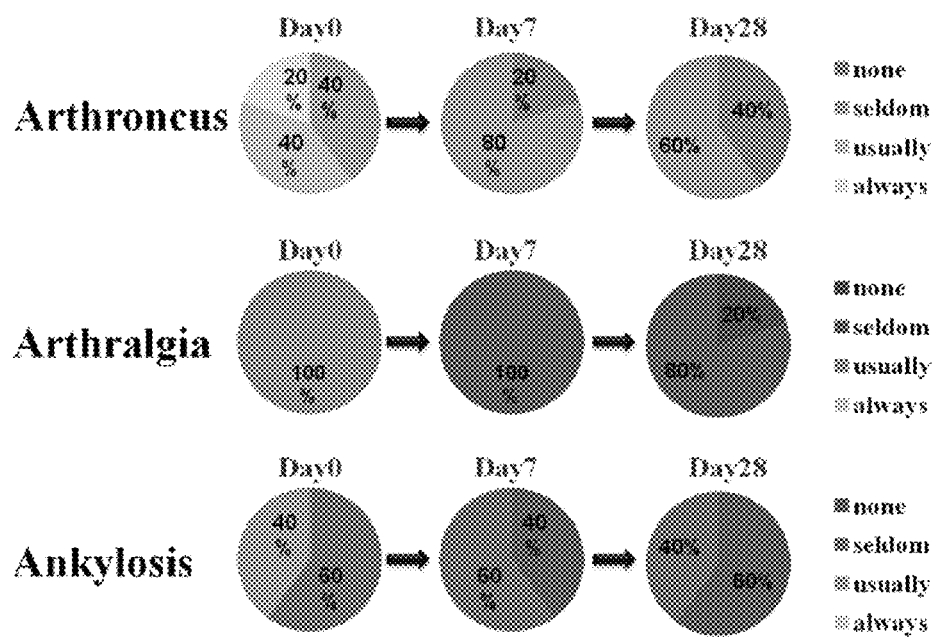
FIG. 8 illustrates the condition of arthroncus, arthralgia and ankylosis in the testers (n=5) administrated *Streptococcus thermophilus* DSM 28121 capsules at 0, 7 and 28.

As shown in FIG. 7, according to the questionnaire, arthroncus, arthralgia and ankylosis in testers were obviously alleviated after ingesting *Streptococcus thermophilus* DSM 28121 capsules for 7 and 28 days. As shown in FIG. 8, on day 7 of the trial, the rates of improvement on arthroncus, arthralgia and ankylosis were 80, 100 and 80%, respectively. The effects lasted to day 28 of the trial, and the rates of improvement were all reached 100%. The frequencies of arthroncus, arthralgia and ankylosis were obviously decreased with the increasing ingestion time.

In addition, in one embodiment, a composition comprises *Streptococcus thermophilus* DSM 28121 for producing hyaluronic acid of the present invention, *Streptococcus thermophilus* DSM 28121 can has activity or inactivity. Moreover, a composition comprises *Streptococcus thermophilus* DSM 28121 or its metabolites can be manufactured into the types of a food product, a health supplement, a medicament or a skin care product. In one embodiment, *Streptococcus thermophilus* DSM 28121 can be used as a material of skin care products, the metabolites produced by fermentation of *Streptococcus thermophilus* DSM 28121 can be homogenized with water phase additives, and then adding an emulsifier mixes well to form a uniform molding formulation making fully use of *Streptococcus thermophilus* DSM 28121, to protect and to enhance the stability of it. *Streptococcus thermophilus* DSM 28121 can be manufactured into a verity of formulations depending on need, such as lotion and cream, but not limited.

In summary, in addition to the bile salt and stomach acid resistance, the intestinal cells adsorption capacity, transporting to intestine and keeping good activity, the probiotic strain of the present invention has the ability of proliferation in intestine to increase the number of strains, and the excellent efficacy of producing hyaluronic acid in intestine, which can be manufactured into a food product, a health supplement, a medicament or a skin care product for effectively enhancing hyaluronic acid, and improving skin, eye and joint health in human body.

What is claimed is:

1. A method of enhancing hyaluronic acid secretion in a subject comprising administrating a composition containing a dose of *Streptococcus thermophilus* DSM 28121 of the sequence of Seq No. 8 twice daily to the subject, wherein the dose comprises $10^3$ CFU to $10^{12}$ CFU of *Streptococcus thermophilus* DSM 28121.

2. The method according to claim 1, wherein *Streptococcus thermophilus* DSM 28121 is isolated from breast milk.

3. The method according to claim 1, wherein *Streptococcus thermophilus* DSM 28121 is a probiotic strain.

4. The method according to claim 1, wherein *Streptococcus thermophilus* DSM 28121 is administrated orally.

5. The method according to claim 1, wherein *Streptococcus thermophilus* DSM 28121 has the ability to survive and colonize in the intestine of the subject to increase the number.

6. The method according to claim 1, wherein the hyaluronic acid content in the blood of the subject is increased.

7. The method according to claim 1, wherein *Streptococcus thermophilus* DSM 28121 is active or inactive.

8. The method according to claim 1, wherein the composition is a food product, a health supplement, a medicament or a skin care product.

9. The method according to claim 8, wherein the composition further comprises a metabolite of *Streptococcus thermophilus* DSM 28121.

10. The method according to claim 1, wherein a skin hydration in the subject is increased.

11. The method according to claim 1, wherein a condition of dry eye in the subject is improved.

12. The method according to claim 1, wherein a condition of arthroncus, arthralgia and ankylosis in the subject is improved.

13. A method of enhancing hyaluronic acid content in the blood in a subject comprising administrating a composition having a dose of *Streptococcus thermophilus* DSM 28121 to the subject,
wherein the dose comprises $10^3$ CFU to $10^{12}$ CFU of *Streptococcus thermophilus* DSM 28121.

14. The method according to claim 13, wherein *Streptococcus thermophilus* DSM 28121 is isolated from breast milk.

15. The method according to claim 13, wherein *Streptococcus thermophilus* DSM 28121 is a probiotic strain.

16. The method according to claim 13, wherein *Streptococcus thermophilus* DSM 28121 has the ability to survive and colonize in the intestine of the subject to increase the number.

17. The method according to claim 13, wherein *Streptococcus thermophilus* DSM 28121 is active or inactive.

18. The method according to claim 13, wherein the composition is a food product, a health supplement, a medicament or a skin care product.

19. The method according to claim 18, wherein the composition further comprises a metabolite of *Streptococcus thermophilus* DSM 28121.

\* \* \* \* \*

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial sequence
<220> FEATURE:
<223> OTHER INFORMATION: synthesized nucleotide sequence

<400> SEQUENCE: 1
agagtttgat cytggytyag                                            20

<210> SEQ ID NO 2
<211> LENGTH: 20
<212> TYPE: DNA
<213> ORGANISM: Artificial sequence
<220> FEATURE:
<223> OTHER INFORMATION: synthesized nucleotide sequence

<400> SEQUENCE: 2
ctttacgccc artrawtccg                                            20

<210> SEQ ID NO 3
<211> LENGTH: 21
<212> TYPE: DNA
<213> ORGANISM: Artificial sequence
<220> FEATURE:
<223> OTHER INFORMATION: synthesized nucleotide sequence

<400> SEQUENCE: 3
caggcctaac acatgcaagt c                                          21

<210> SEQ ID NO 4
<211> LENGTH: 23
<212> TYPE: DNA
<213> ORGANISM: Artificial sequence
<220> FEATURE:
<223> OTHER INFORMATION: synthesized nucleotide sequence

<400> SEQUENCE: 4
tggagagttt gatcctggct cag                                        23

<210> SEQ ID NO 5
<211> LENGTH: 20
<212> TYPE: DNA
<213> ORGANISM: Artificial sequence
<220> FEATURE:
```

<223> OTHER INFORMATION: synthesized nucleotide sequence

<400> SEQUENCE: 5
ggactaccag ggtatctaat                                        20

<210> SEQ ID NO 6
<211> LENGTH: 19
<212> TYPE: DNA
<213> ORGANISM: Artificial sequence
<220> FEATURE:
<223> OTHER INFORMATION: synthesized nucleotide sequence

<400> SEQUENCE: 6
gtgccagcag ccgcggtaa                                         19

<210> SEQ ID NO 7
<211> LENGTH: 20
<212> TYPE: DNA
<213> ORGANISM: Artificial sequence
<220> FEATURE:
<223> OTHER INFORMATION: synthesized nucleotide sequence

<400> SEQUENCE: 7
aggcccggga acgtattcac                                        20

<210> SEQ ID NO 8
<211> LENGTH: 420
<212> TYPE: DNA
<213> ORGANISM: Streptococcus thermophilus

<400> SEQUENCE: 8
ttcaggcggt tagaggttcg tctcctctag ggtgcatttt tatcgggaag tagctcagca      60
tggtagagca cttggtttgg gaccaagggg tcgcaggttc caatcctgtc ttcccgatta     120
agacctttga taactgaata agaaaccaag tgcagggtta tgatagaaga attataacct     180
gtcaatttac aagaataaat cgtcagacga cggtaatgag ttaacgctcg aacaattatt     240
aaagtattaa tgagagtttg atcctggctc aggacgaacg gtggcggcgt gcctaataca     300
tgcaagtaga acgctgaaga gaggagcttg ctcttcttgg atgagttgcg aacgggtgag     360
taacgcgtag ctaacctgcc ttgtagcggg ggataactat tggaaacgat agctaatacc     420